(12) United States Patent
Liang et al.

(10) Patent No.: US 8,481,448 B2
(45) Date of Patent: Jul. 9, 2013

(54) CATALYST FOR OXIDATION OF SATURATED AND UNSATURATED ALDEHYDES TO UNSATURATED CARBOXYLIC ACID, METHOD OF MAKING AND METHOD OF USING THEREOF

(75) Inventors: Wugeng Liang, Elgin, IL (US); David Sullivan, Sugar Land, TX (US); James W. Kauffman, Katy, TX (US); Clark Rea, Houston, TX (US); Joe Linzer, Issaquah, WA (US); Shahid Shaikh, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 279 days.

(21) Appl. No.: 12/838,863

(22) Filed: Jul. 19, 2010
(Under 37 CFR 1.47)

(65) Prior Publication Data
US 2012/0016159 A1    Jan. 19, 2012

(51) Int. Cl.
*B01J 21/00* (2006.01)
*B01J 23/00* (2006.01)
*B01J 23/32* (2006.01)
*B01J 27/00* (2006.01)
*B01J 27/185* (2006.01)
*B01J 27/188* (2006.01)
*B01J 27/19* (2006.01)
*B01J 27/192* (2006.01)
*B01J 27/198* (2006.01)
*C07C 51/16* (2006.01)
*C07C 51/235* (2006.01)

(52) U.S. Cl.
USPC ........... 502/209; 502/208; 502/210; 502/211; 502/212; 502/213; 502/240; 502/241; 502/242; 502/243; 502/246; 502/247; 502/248; 502/249; 502/305; 502/307; 502/309; 502/310; 502/311; 502/312; 502/317; 502/319; 502/321; 502/324; 502/353; 562/531; 562/532; 562/535

(58) Field of Classification Search
USPC .. 502/208–213, 240–263, 305–355; 562/531, 562/532, 535
See application file for complete search history.

(56) References Cited

U.S. PATENT DOCUMENTS

| | | | |
|---|---|---|---|
| 3,541,143 A | 11/1970 | Nakano et al. | |
| 3,998,876 A | 12/1976 | Kato et al. | |
| 4,388,223 A | 6/1983 | Ferlazzo et al. | |
| 4,444,907 A * | 4/1984 | Ohdan et al. | 502/211 |
| 4,495,109 A | 1/1985 | Grasselli et al. | |
| 5,198,579 A | 3/1993 | Honda et al. | |
| 5,206,431 A | 4/1993 | Hashiba et al. | |
| 5,420,091 A * | 5/1995 | Kuroda et al. | 502/209 |
| 5,532,199 A | 7/1996 | Watanabe et al. | |
| 5,550,095 A | 8/1996 | Naito et al. | |
| 5,618,974 A | 4/1997 | Kurimoto et al. | |
| 6,946,422 B2 | 9/2005 | Stevenson et al. | |
| 7,045,482 B2 | 5/2006 | Chun et al. | |
| 7,485,596 B2 * | 2/2009 | Kauffman et al. | 502/212 |
| 7,649,111 B2 | 1/2010 | Liang et al. | |
| 7,649,112 B2 | 1/2010 | Stevenson et al. | |
| 7,732,367 B2 * | 6/2010 | Stevenson et al. | 502/208 |
| 7,825,061 B2 * | 11/2010 | Sudo et al. | 502/208 |
| 7,923,404 B2 * | 4/2011 | Stevenson et al. | 502/208 |
| 7,999,133 B2 * | 8/2011 | Stevenson et al. | 562/512.2 |
| 8,232,224 B2 * | 7/2012 | Liang et al. | 502/208 |
| 2006/0041168 A1 * | 2/2006 | Naitou et al. | 562/535 |
| 2007/0021629 A1 | 1/2007 | Stevenson et al. | |
| 2007/0149388 A1 | 6/2007 | Kauffman et al. | |
| 2007/0149806 A1 * | 6/2007 | Liang et al. | 562/535 |
| 2008/0188681 A1 | 8/2008 | Liang et al. | |
| 2011/0143931 A1 * | 6/2011 | Liang et al. | 502/205 |

FOREIGN PATENT DOCUMENTS
WO    2007073492 A1    6/2007

OTHER PUBLICATIONS

International Search Report; International Application No. PCT/US2011/043624; International Filing Date: Jul. 12, 2011; Date of Mailing: Sep. 22, 2011; 5 Pages.
Written Opinion of the International Searching Authority; International Application No. PCT/US2011/043624; International Filing Date: Jul. 12, 2011; Date of Mailing: Sep. 22, 2011; 6 Pages.
Concise Chemical and Technical Dictionary; H. Bennet, Ed.; Third Enlarged Edition; p. 949; Chemical Publishing Co., Inc. (1974).
Concise Chemical and Technical Dictionary; H. Bennet, Ed.; Third Enlarged Edition; p. 964; Chemical Publishing Co., Inc. (1974).
CRC Handbook of Physics and Chemistry; D. R. Lide, Ed.; pp. 4-47; 81st Edition (2000).
The Merck Index; S. Budavari, Ed.; Twelfth Edition; pp. 211-213; Merck Research Laboratories (1996).

* cited by examiner

*Primary Examiner* — Patricia L Hailey
(74) *Attorney, Agent, or Firm* — Cantor Colburn LLP

(57) ABSTRACT

The invention is a heteropoly acid compound catalyst composition, a method of making the catalyst composition and a process for the oxidation of saturated and/or unsaturated aldehydes to unsaturated carboxylic acids using the catalyst composition. The catalyst composition is a heteropoly acid compound containing molybdenum, vanadium, phosphorus, cesium, bismuth, copper and antimony. Thermal stability is achieved with higher cesium content (up to less than 3.0) but antimony, copper and bismuth must be present to maintain good activity.
The catalyst is made by dissolving compounds of the components of each of the heteropoly acid compounds in a solution, precipitating the heteropoly acid compounds, obtaining a catalyst precursor and calcining the catalyst precursor to form a heteropoly acid compound catalyst.
Unsaturated aldehydes, such as methacrolein, may be oxidized in the presence of the heteropoly acid compound catalyst to produce an unsaturated carboxylic acid, such as methacrylic acid.

20 Claims, 7 Drawing Sheets

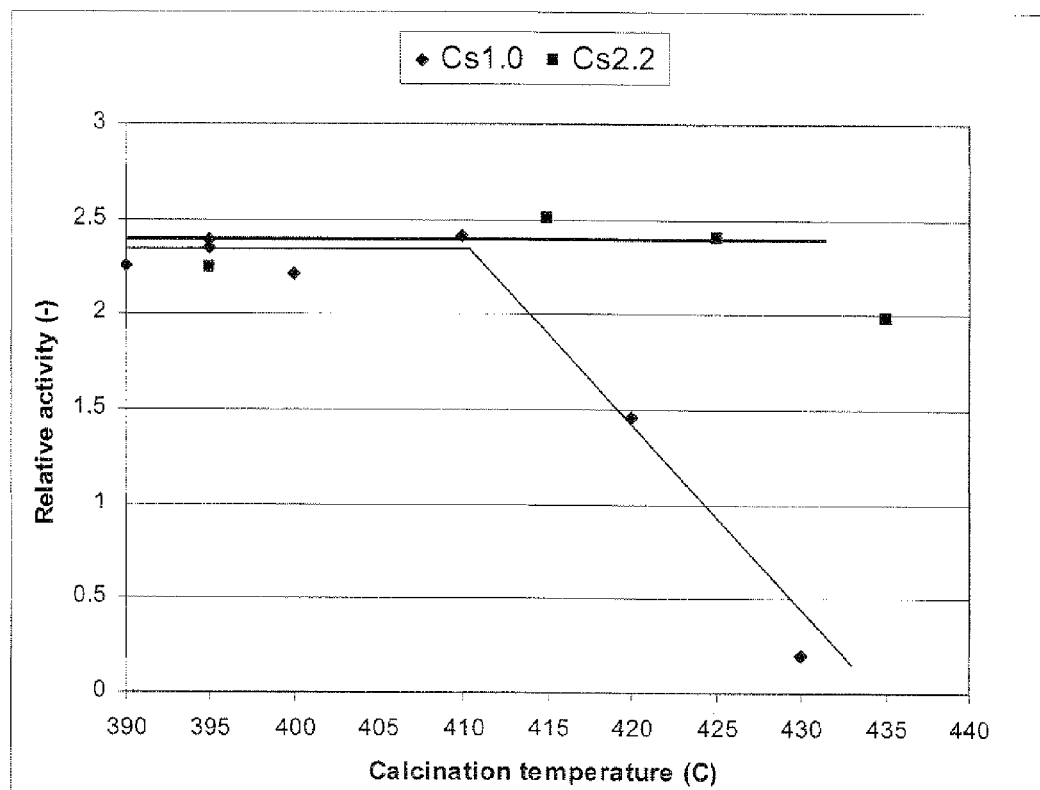
Figure 1. Catalytic activities obtained from high and low Cs content catalysts under different calcination temperatures.

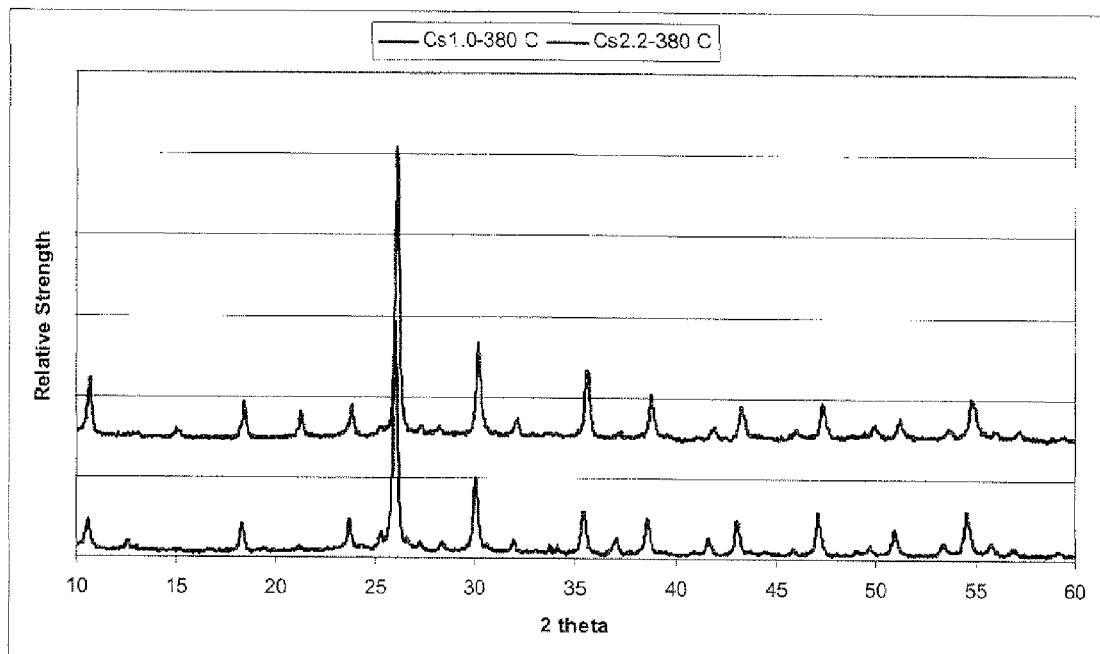
Figure 2. XRD of low Cs content and high Cs content catalysts at 380°C.

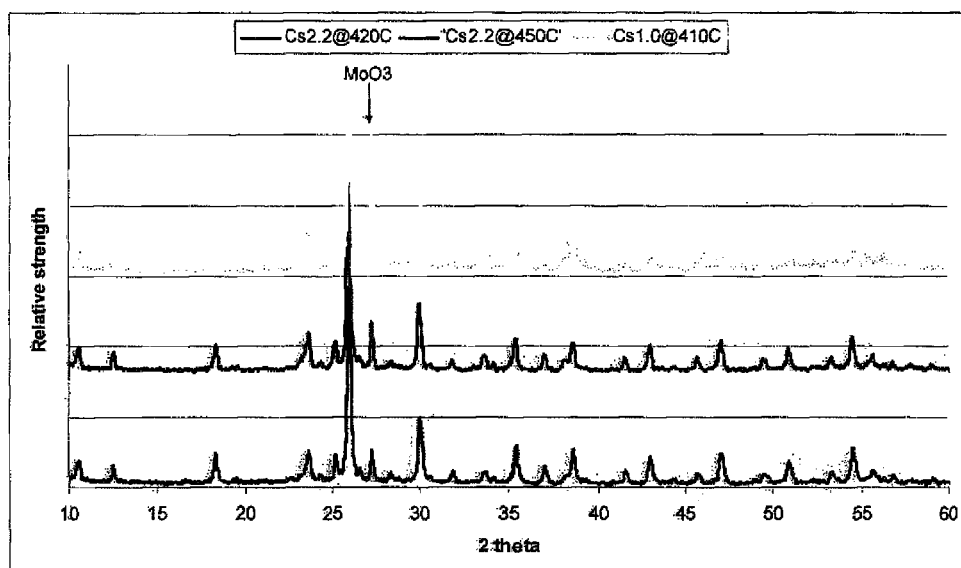
Figure 3. XRD of low Cs content and high Cs content catalysts at different temperatures.

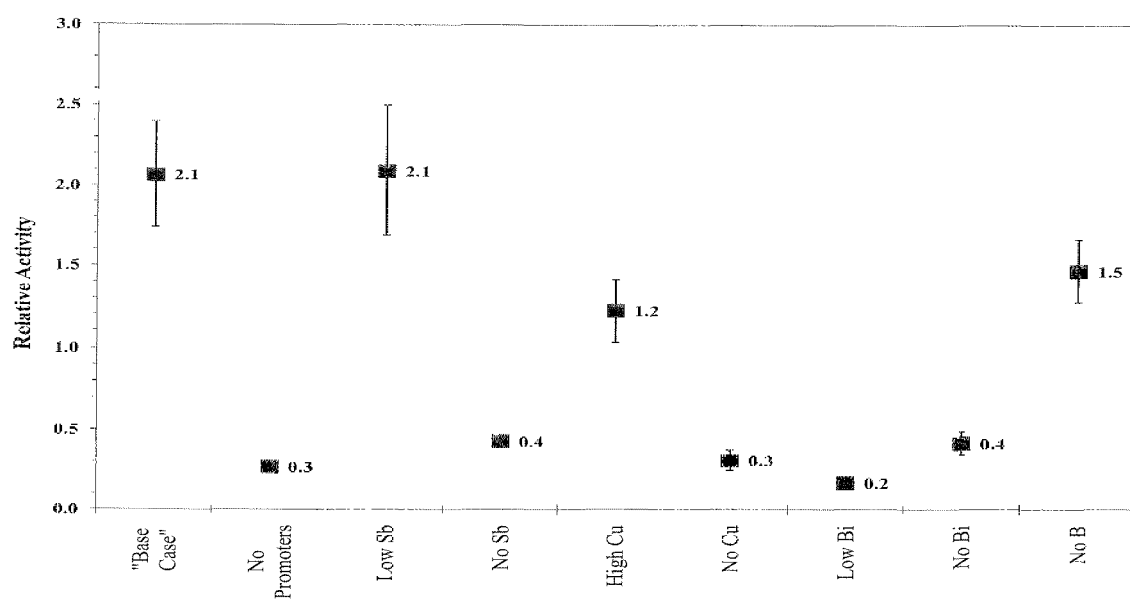
Figure 4. Comparison of Catalyst Activities of HPAs with various promoters.

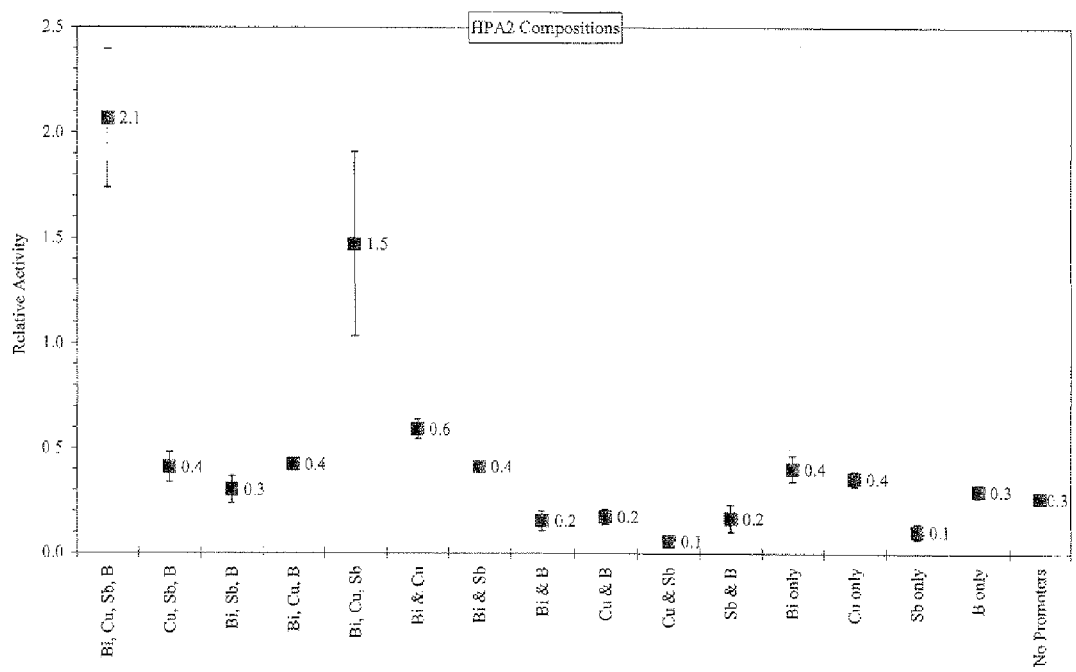
Figure 5. Comparison of Catalyst Activities of HPAs with various promoters.

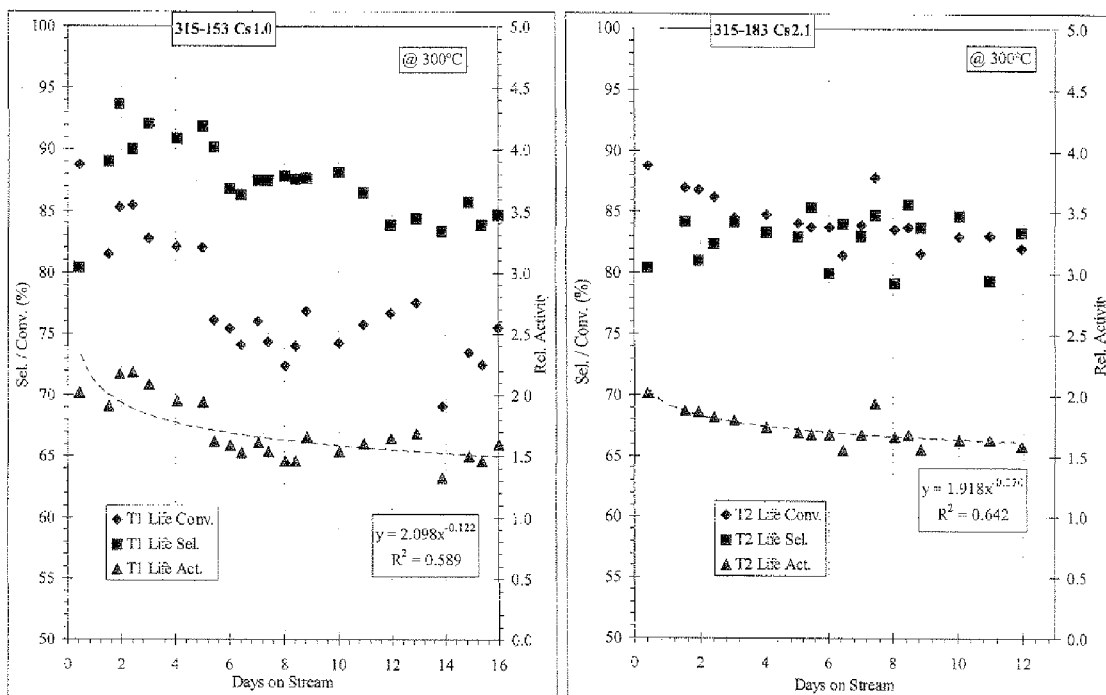
Figure 6A-1. Lifetime tests of low Cs catalyst.
Figure 6A-2. Lifetime tests of high Cs catalyst.

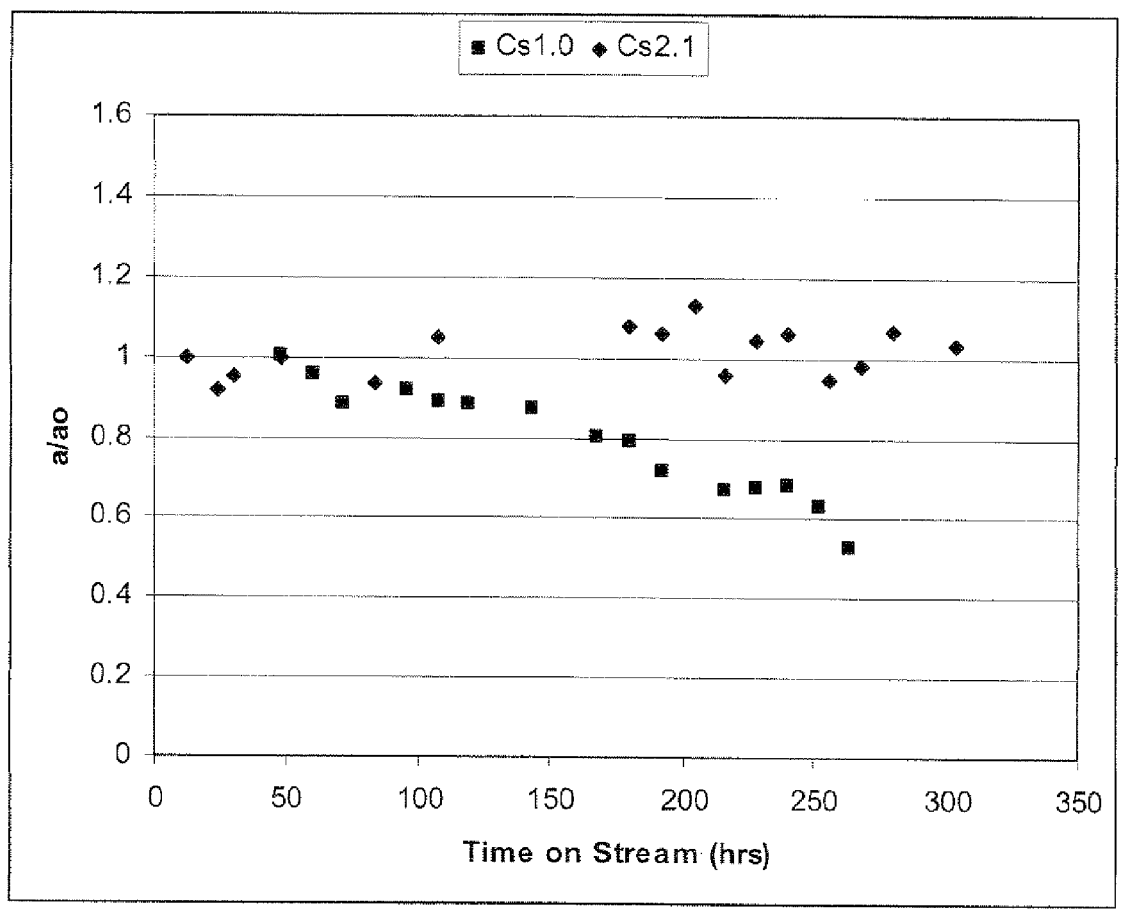
Figure 6B. Lifetime tests of low Cs and high Cs catalysts.

CATALYST FOR OXIDATION OF SATURATED AND UNSATURATED ALDEHYDES TO UNSATURATED CARBOXYLIC ACID, METHOD OF MAKING AND METHOD OF USING THEREOF

BACKGROUND OF THE INVENTION

1. Field of the Invention

This invention relates to heteropoly acid catalyst compositions, a method of making such catalyst compositions and a process for the oxidation of unsaturated aldehydes, such as methacrolein, to unsaturated carboxylic acids, such as methacrylic acid, in a vapor phase reaction using such catalyst compositions.

2. Description of the Prior Art

Various catalysts are known for the gas phase catalytic oxidation of unsaturated aldehydes to unsaturated carboxylic acids. Included are molybdenum-based mixed metal oxides compound which can contain oxides of metals such as phosphorus, arsenic, cesium, rubidium, cobalt, nickel, iron, chromium, antimony, tellurium and silicon in addition to molybdenum. These same metals and others may occur in heteropoly acid compounds as metal oxide clusters forming heteropolyoxoanions in acid form instead of simple metal oxides. Heteropoly acid compounds are also known as catalysts for the gas phase catalytic oxidation of unsaturated aldehydes to unsaturated carboxylic acids. Heteropoly acid compounds have a central metal atom surrounded by a framework of other metal atoms connected to each other and the central metal atom through oxygen atoms. The central metal atom is different ("hetero") from the framework metal atoms.

One problem of heteropoly acid compounds as catalysts is thermal stability. In process operating temperatures, the heteropoly acid compound catalysts tend to deactivate by chemically and physically breaking down. Commercially useful heteropoly acid compound catalysts compound catalysts must have thermal stability for acceptable catalyst lifetime.

SUMMARY OF THE INVENTION

The present invention is for a heteropoly acid catalyst composition, a method of making the catalyst composition and a process of using the catalyst composition for the oxidation of unsaturated aldehydes, such as methacrolein, to unsaturated carboxylic acids, such as methacrylic acid, in a vapor phase reaction. The catalyst composition has the general formula $Mo_{12}V_aP_bCs_cBi_dCu_eSb_fO_x$, where Mo is molybdenum, V is vanadium, P is phosphorus, Cs is cesium, Bi is bismuth, Cu is copper, Sb is antimony and O is oxygen, a is 0.01 to 5.0, b is 0.5 to 3.5, c is 1.5 to 2.75, d is 0.05 to 0.5, e is 0.05 to 0.5, f is 0.1 to 0.5 and x satisfies the valences. Presence of cesium along with bismuth, copper and antimony is required for a heteropoly acid compound catalyst with good thermal stability and catalytic performance. This catalyst composition is essentially insoluble in water.

In general, the method of making the catalyst is to dissolve compounds of the catalyst components of the heteropoly acid compound in an acidified aqueous solution, precipitating particles of the catalyst precursor, drying the solid particles and calcining the solid particles.

In general, the process of using the catalyst compositions for the oxidation of unsaturated aldehydes to unsaturated carboxylic acids in a vapor phase reaction is to contact the unsaturated aldehyde, such as methacrolein, with an oxidizing agent, such as air or another oxygen-containing gas, in the presence of the heteropoly acid compound catalyst at conditions to produce an unsaturated carboxylic acid, such as methacrylic acid.

BRIEF DESCRIPTION OF THE DRAWINGS

A more complete appreciation of the invention and many of the attendant advantages thereof will be readily understood by reference to the following detailed description when considered in connection with the accompanying drawings wherein:

FIG. 1 shows catalytic activities obtained from high and low Cs content catalysts under different calcination temperatures FIG. 2 shows XRD of low Cs content and high Cs content catalysts at 380° C.

FIG. 3 shows XRD of low Cs content and high Cs content catalysts at different temperatures FIG. 4 shows a comparison of catalyst activities of heteropoly acid compound catalysts with various promoters.

FIG. 5 shows a comparison of catalyst activities of heteropoly acid compound catalysts with various promoters.

FIG. 6A-1 shows lifetime tests of low Cs catalyst.

FIG. 6A-2 shows lifetime tests of high Cs catalyst.

FIG. 6B shows lifetime tests of low Cs and high Cs catalysts.

DETAILED DESCRIPTION OF THE INVENTION

Heteropoly acid compounds are known as catalysts for the oxidation of unsaturated aldehydes, such as methacrolein, to unsaturated carboxylic acids, such as methacrylic acid, in a vapor phase reaction. The presence of an alkali metal, such as potassium, rubidium, cesium or sodium, in a heteropoly compound can be beneficial for improvement of thermal strength. However, as the amount of alkali metal increases, catalyst performance, both activity and selectivity, decreases. A catalyst composition with improved thermal stability while maintaining catalytic performance for methacrolein oxidation to methacrylic acid would be advantageous for commercial development of heteropoly acid compounds catalysts for the oxidation of unsaturated aldehydes, such as methacrolein, to unsaturated carboxylic acids, such as methacrylic acid. The catalyst of the present invention is a heteropoly acid compound of the general formula $Mo_{12}V_aP_bCs_cBi_dCu_eSb_fO_x$ where Mo is molybdenum, V is vanadium, P is phosphorus, Cs is cesium, Bi is bismuth, Cu is copper, Sb is antimony and O is oxygen, a is 0.01 to 5.0, b is 0.5 to 3.5, c is 1.5 to 2.75, d is 0.05 to 0.5, e is 0.05 to 0.5, f is 0.1 to 0.5 and x satisfies the valences.

The heteropoly acid compound may contain additional elements, such as boron, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum. One embodiment of the heteropoly acid compound has the general formula $Mo_{12}V_aP_bCs_cBi_dCu_eSb_fM'_gO_x$ where Mo is molybdenum, V is vanadium, P is phosphorus, Cs is cesium, Bi is bismuth, Cu is copper, Sb is antimony, M' is one or more of boron, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum, O is oxygen, a is 0.01 to 5.0, b is 0.5 to 3.5, c is 1.5 to 2.75, d is 0.05 to 0.5, e is 0.05 to 0.5, f is 0.1 to 0.5, g is 0 to 0.5 and x satisfies the valences.

In other embodiments of the invention, a is 0.1 to 1.0, 0.3 to 0.6 or about 0.5; b is 1.0 to 2.0, 1.25 to 1.75 or about 1.5; c is less than about 3.0, 1.5 to 2.5, 2.0 to 2.5 or about 2.1, d is 0.1 to 0.4, 0.1 to 0.2 or about 0.15, e is 0.05 to 0.3 or 0.1 to 0.3 or about 0.1, f is 0.1 to 0.4, 0.1 to 0.3 or about 0.3 and g is 0 to 0.4, 0.1 to 0.4 or about 0.3.

The method of making the heteropoly acid compound. Compounds containing the elements of the particular heteropoly acid compound are dissolved in a liquid which may be aqueous, aqueous/organic mixtures or organic. The liquid is preferably aqueous. The liquid is acidified to promote dissolution of the compounds. The acid may be organic, such as acetic acid, or inorganic, such as nitric acid. The acidity of the liquid may be completely or partially neutralized by the addition of a base, such as an ammonium-containing compound, e.g. ammonium hydroxide. Precipitation may occur spontaneously as the compounds are mixed together in solution or it may be promoted by heating, cooling or other changes in ambient conditions or by adding a material which will act as a nucleus or "seed" for precipitation of particles. This "seed" material can be a compound containing one or more of the elements of the catalyst composition. After precipitating solid particles, the liquid is removed, e.g., evaporation, and the solid particles are dried and calcined.

Suitable molybdenum compounds are, but not limited to, ammonium paramolybdate, molybdenum trioxide, molybdenum chloride or mixtures or combinations thereof.

Suitable vanadium components are, but not limited to, ammonium metavanadate, vanadium pentoxide, vanadium chloride or mixtures or combinations thereof.

Suitable phosphorus compounds are, but not limited to, phosphoric acid, ammonium phosphite or mixtures or combinations thereof.

Suitable copper compounds are, but not limited to, copper nitrate, copper chloride or mixtures or combinations thereof.

Suitable bismuth compounds are, but not limited to, bismuth nitrate, bismuth oxide, bismuth chloride or mixtures or combinations thereof.

Suitable boron compounds are, but not limited to, boric acid, boric acid salts, boric oxide, borate esters or mixtures or combinations thereof.

Suitable potassium, rubidium, cesium and sodium compounds are, but not limited to, nitrates, oxides, chlorides or mixtures or combinations thereof.

Suitable antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum compounds are, but not limited to, nitrates, oxides, chlorides or mixtures or combinations thereof.

One purpose of calcination of the catalyst precursor is to activate the catalyst by obtaining an oxide of the metal components. The catalyst precursor may be calcined at a temperature of about 350° C. to about 450° C. for about 2 to about 12 hours. The calcination may be in two stages, one at a temperature lower than about 350° C. for about 1 to about 8 hours and another at a temperature above about 350° C. for about 2 to about 12 hours. Calcination may be done in a high temperature oven or kiln.

The process of using the present invention is to contact feedstock containing saturated and/or unsaturated aldehydes with an oxidizing agent in the presence of the heteropoly acid compound catalyst in a vapor phase reaction at reaction conditions to produce an unsaturated carboxylic acid. In one embodiment of the present invention, the feedstock for this process is an unsaturated aldehyde, such as methacrolein, which is the product of an oxidation reaction of an olefin, such as isobutylene, and may contain a recycle of the oxidation of the unsaturated aldehyde, such as methacrolein, to unsaturated carboxylic acids, such as methacrylic acid. Therefore, the feedstock contains, in addition to unsaturated aldehydes, unreacted reactants, inerts and byproducts, such as water, oxygen, nitrogen, carbon monoxide, carbon dioxide, noble gases, acetone, acetic acid, acrolein, methacrylic acid, isobutylene, and other olefins and saturated and unsaturated hydrocarbons. The concentration of unsaturated aldehydes in the feedstock may vary over a wide range. Examples of the concentration of methacrolein are from about 1 vol. % to about 20 vol. % or from about 2 vol. % to about 8 vol. %.

In another embodiment of the present invention, the feedstock contains products and byproducts from a process for hydroformylation of an olefin, such as propylene, to saturated aldehydes, such as butanals, e.g., n-butanal and isobutanal or isobutyraldehyde. In another embodiment of the present invention, the feedstock contains a combination of saturated and unsaturated aldehydes in proportions from about 5 wt % to about 95 wt %. Embodiments of the present invention having saturated aldehydes in the feedstock are described in U.S. Pat. Nos. 7,649,111 and 7,649,112 which are hereby incorporated by reference.

The oxidizing agent may be air or another oxygen-containing gas. There may be gases or vapors other than oxygen, such as nitrogen, carbon dioxide, noble gases and steam, in the oxidizing agent. The oxidizing agent may be pure oxygen. In one embodiment of the process of the present invention, the amount of oxygen relative to aldehyde would be from 40% less than stoichiometric to 700% more than stoichiometric on a molar basis, preferably 60% more than stoichiometric to 360% more than stoichiometric on a molar basis. In another embodiment of the process of the present invention in which the aldehyde is methacrolein, the amount of oxygen relative to methacrolein is from about 0.3 to about 4, preferably from about 0.8 to about 2.3 by mole ratio.

The process conditions are at a pressure from about 0 atm to about 5 atm, preferably at about 1 atm, and at a temperature from about 230° C. to about 450° C., preferably 250° C. to about 400° C., more preferably about 250° C. to about 350° C.

The reactor for the process of the present invention may be any reactor for a vapor phase reaction, such as a fixed bed reactor, a fluidized bed reactor or a moving bed reactor.

The invention having been generally described, the following examples are given as particular embodiments of the invention and to demonstrate the practice and advantages thereof. It is understood that the examples are given by way of illustration and are not intended to limit the specification or the claims to follow in any manner.

In all of the examples, the catalyst activities reported were adjusted by taking into account differences in methacrolein conversion, reaction temperature and space velocity, due to differences in amount of catalyst or gas flow rate, by assuming that the reaction is net first order in methacrolein concentration and follows an arrhenius-type temperature dependence. Activities of the catalysts are reported relative to a catalyst for which 3.0 cc of catalyst and 50 sccm total flowrate gave 94.1% conversion and 91.7% selectivity at 284° C. The relative activity of this catalyst is defined as 1.0. If a catalyst showed an activity 50% higher than this reference catalyst, then the catalyst would have a relative activity of 1.5.

It is well known that selectivity for methacrolein oxidation (and indeed most partial oxidation reactions) is dependent on methacrolein conversion, i.e., as conversion is increased the selectivity decreases due to further oxidation of the desired products. Given this, the selectivities of two different catalysts must be compared at the same conversion for the comparison to be meaningful. The selectivity of a reference heteropoly acid compound catalyst was measured across a wide range of conversions, from about 65% to about 97% and a curve was fit to this data over that range. The actual selectivities of the following Examples were compared to the selectivity curve that was generated for the reference heteropoly acid compound catalyst at the same conversion. The absolute percent difference between the selectivities of the catalysts of the Examples and the selectivity of the reference heteropoly acid compound catalyst at the same conversion is reported as "relative selectivity". If the catalyst showed a selectivity 1.0% higher than the reference heteropoly acid compound catalyst at the same conversion, then this catalyst would have a relative selectivity of 1.0.

Example 1

Ammonium paramolybdate (46.92 g) is added to 200 ml de-ionized (DI) water at room temperature. Ammonium metavanadate (1.29 g.) is added to above solution. The mixture is stirred at room temperature and all particles are dissolved. Cesium nitrate (8.63 g.) is added to 50 ml DI water, and the solution is added to above solution. Phosphoric acid (3.83 g.) dissolved in 6 ml DI water is added to above solution. Copper nitrate (0.51 g.) is added to 5 ml DI water and the solution obtained is added into the above solution. Nitric acid (11.33 g.) is added to DI water (30 g.), then 7 ml NH$_4$OH (28%) is added into this solution, and then bismuth nitrate (1.61 g.) is added to the solution and dissolved. This bismuth nitrate solution is added to the above solution. The mixture temperature is increased to 95° C. Then, antimony trioxide (0.97 g.) is added to above mixture and boric acid (0.41 g.) is added to above mixture.

The mixture is evaporated at 100° C., dried at 130° C. for 16 hrs, and sieved to obtain 20-30 mesh particles. The particles are calcined at 395° C. for 5 hrs under air. A catalyst with composition of $Mo_{12}V_{0.5}P_{1.5}Cs_{2.0}Bi_{0.15}Cu_{0.1}Sb_{0.3}B_{0.3}$ is obtained.

3.0 cc of the calcined material is loaded in the reactor and the reaction is carried out. A relative activity of 2.5 is obtained, as shown in Table 1.

Example 2 to 4

Examples 2 to 4 are prepared by following the method shown in Example 1, but with different Cs content. Their performances obtained are given in Table 1. From these examples, it can be seen that the catalytic activities obtained from catalysts of this invention are much higher than that obtained from catalysts of patent art as discussed above.

Comparative Example 1

A catalyst with composition of $Mo_{12}V_{0.5}P_{1.5}Cs_{3.0}Cu_{0.1}Sb_{0.3}B_{0.3}$ is prepared with the method shown in Example 1. It can be seen that the Cs content in this catalyst is very high, $Cs3.0$. It is tested by the same way as Example 1 and a relative activity of 0.1 is obtained. It indicates that there is an upper limit of Cs content in the catalyst.

TABLE 1

| Catalytic performance of catalysts with high Cs content | | |
|---|---|---|
| Examples | Composition | Relative Activity |
| Ex. 1 | $Mo_{12}V_{0.5}P_{1.5}Cs_{2.0}Bi_{0.15}Cu_{0.1}Sb_{0.3}B_{0.3}$ | 2.5 |
| Ex. 2 | $Mo_{12}V_{0.5}P_{1.5}Cs_{2.1}Bi_{0.15}Cu_{0.1}Sb_{0.3}B_{0.3}$ | 2.5 |
| Ex. 3 | $Mo_{12}V_{0.5}P_{1.5}Cs_{2.2}Bi_{0.15}Cu_{0.1}Sb_{0.3}B_{0.3}$ | 2.3 |
| Ex. 4 | $Mo_{12}V_{0.5}P_{1.5}Cs_{2.5}Bi_{0.05}Cu_{0.1}Sb_{0.3}B_{0.3}$ | 1.0 |
| Com-Ex. 1 | $Mo_{12}V_{0.5}P_{1.5}Cs_{3.0}Cu_{0.1}Sb_{0.3}B_{0.3}$ | 0.1 |

The following examples are used to show the higher thermal stability of the new catalyst comparing catalysts with low monovalent content heteropoly compound. The comparison is carried out by comparing catalytic activities and selectivities obtained from a catalyst with high Cs content and a catalyst with low Cs content after calcining under different temperatures. Catalyst obtained from Example 3 is used as the high Cs content catalyst. The lower Cs content catalyst is obtained by the following example.

Comparative Example 2

Ammonium paramolybdate (46.49 g.) is added to 200 ml de-ionized (DI) water at room temperature. Ammonium metavanadate (1.28 g.) is added to above solution. The mixture is stirred at room temperature and all particles are dissolved. Cesium nitrate (4.28 g.) is added to 25 ml DI water, and the solution is added to above solution. Phosphoric acid (3.80 g.) dissolved in 6 ml DI water is added to above solution. Copper nitrate (0.51 g.) is added to 5 ml DI water and the solution obtained is added into the above solution. Nitric acid (11.32 g.) is added to DI water (30 g.), then 7 ml NH$_4$OH (28%) is added into this solution, and then bismuth nitrate (5.32 g.) is added to the solution and dissolved. This bismuth nitrate solution is added to the above solution. The mixture temperature is increased to 95° C. Then, antimony trioxide (2.56 g.) is added to above mixture and boric acid (0.68 g.) is added to above mixture.

The mixture is evaporated at 100° C., dried at 130° C. for 16 hrs, and sieved to obtain 20-30 mesh particles. A catalyst with composition of $Mo_{12}Cs_{1.0}Bi_{0.5}P_{1.5}Cu_{0.1}V_{0.5}Sb_{0.8}B_{0.5}O_x$ is obtained after calcination, which has Cs content 1.0.

These two catalysts are calcined under different temperatures and their testing results obtained are plotted in FIG. 1. At a lower calcination temperature, like 395° C., both catalysts give very high performance.

For low Cs content catalyst, when it is calcined above 410° C., like at 420° C., a much lower activity (1.4) is obtained, due to its lower thermal stability. For high Cs content catalyst, even when it calcined at 425° C., a very high performance (2.4) is still obtained. When the low Cs catalyst is calcined at 430° C., only an activity of 0.2 is obtained, indicating the severe degradation of the catalyst structure. More discussion on the structure change will be given later. For high Cs catalyst, after 435° C. calcination, a very high activity of 2.0 is still obtained, indicating its higher thermal stability.

The relative selectivities obtained with $Cs_{1.0}$ and $Cs_{2.2}$ under different calcination temperatures are shown in Table 2. It can be seen that for low Cs catalyst, after it is calcined at 430° C., due to the structure degradation, a significantly lower selectivity is obtained. But, for a high Cs content catalyst, due to its higher thermal stability, after 435° C. calcination, no loss in selectivity is observed.

TABLE 2

Selectivity comparison of catalysts with high and low Cs content

| Calcination Temp. (C.) | Low Cs | Calcination temp (C.) | High Cs |
|---|---|---|---|
| 395 | 0 | 395 | 0 |
| 410 | 0 | 415 | 0 |
| 420 | 0 | 425 | 0 |
| 430 | −5 | 435 | 0 |

The XRD data of these two catalysts with different Cs contents under different calcination temperatures are shown in FIGS. 2 and 3. It should be noted that the temperature shown in FIGS. 2 and 3 is the temperature in the XRD cell under which the data was collected. This is different from the temperature shown in FIG. 1, which is the catalyst bed temperature under which these catalysts are calcined in the calcination furnace with air flow. But the trend is the same.

For catalysts under 380° C. treatment, both catalysts show complete Keggin crystal structure, as shown in FIG. 2. This is consistent with the high performance observed when both catalysts are calcined under a lower temperature, as shown in FIG. 1.

But when the catalyst with $Cs_{1.0}$ is treated at 410° C., a large amount of $MoO_3$ is formed, which is shown by the XRD peak at about 2T, indicating a significant Keggin structure degradation, as shown in FIG. 3. For catalyst with $Cs_{2.2}$, when it is treated at 420° C., the amount of $MoO_3$ formed is much less than that of $Cs_{1.0}$ at 410° C. Even under 450° C., $MoO_3$ formation with $Cs_{2.2}$ is clearly less than that of $Cs_{1.0}$ under 410° C., indicating that the low Cs content catalyst loses its heteropoly compound crystal structure much easier than the high Cs content catalyst. Therefore, a much stronger thermal stability is achieved with high Cs content catalyst. Due to its crystal structure degradation, the low Cs content catalyst loses its catalytic performance at a much lower calcination temperature, as indicated in FIG. 1 and Table 2.

Therefore, the catalyst composition invented in this disclosure will give both high catalytic performance and high thermal stability, which is not seen from current patent art.

The catalyst compositions shown in Table 3 were prepared to see the effects of the promoter elements (B, Cu, Sb, Bi) and of the alkali-metals (Cs, K, Rb). The preparations were varied on the bases of amounts of alkalis and promoters added during catalyst preparation. Table 3 also shows the relative activities of these various catalysts. The activities for these high-Cs heteropoly acid compound catalysts are further compared in FIGS. 4 and 5.

The results clearly show that these high-Cs heteropoly acid compound catalysts need the presence of Sb, Cu, and Bi in order to give high activity. The absence of any one of these three promoters produces a catalyst with activity less than 0.5. The amount of Sb in the high-Cs heteropoly acid compound catalyst may be reduced somewhat; the $Sb_{0.1}$ catalyst showed activity equal to that of $Sb_{0.3}$ catalyst. On the other hand, the amount of Bi may not be reduced. While the amount of Cu may be increased and still show a decent activity, it appears that $Cu_{0.1}$ is near the optimum amount to produce the best activity.

The results also show that only heteropoly acid compound catalysts with Cs produce good activity. The substitution of Cs with the other alkali metals, K and Rb, produces catalysts with poor activity.

These results give us enough information to claim a composition of high-alkali content heteropoly acid compounds catalyst which not only has good thermal stability, but also has good activity. The need to use Cs as the alkali metal and to use all three promoters (Bi, Cu, and Sb) will differentiate our patent claims versus those shown in Table 1.

TABLE 3

Detailed Catalyst Study.

| Catalyst Description | Mo | V | P | Cs | Bi | Cu | Sb | B | Relative Activity |
|---|---|---|---|---|---|---|---|---|---|
| Base case | 12 | 0.5 | 1.5 | 2.1 | 0.15 | 0.1 | 0.3 | 0.3 | 2.1 |
| Low Bi | 12 | 0.5 | 1.5 | 2.1 | 0.05 | 0.1 | 0.3 | 0.3 | 0.2 |
| No Bi | 12 | 0.5 | 1.5 | 2.1 | 0.0 | 0.1 | 0.3 | 0.3 | 0.4 |
| High Cu | 12 | 0.5 | 1.5 | 2.1 | 0.15 | 0.3 | 0.3 | 0.3 | 1.2 |
| No Cu | 12 | 0.5 | 1.5 | 2.1 | 0.15 | 0.0 | 0.3 | 0.3 | 0.3 |
| Low Sb | 12 | 0.5 | 1.5 | 2.1 | 0.15 | 0.1 | 0.1 | 0.3 | 2.1 |
| No Sb | 12 | 0.5 | 1.5 | 2.1 | 0.15 | 0.1 | 0.0 | 0.3 | 0.4 |
| No B | 12 | 0.5 | 1.5 | 2.1 | 0.15 | 0.1 | 0.3 | 0.0 | 1.5 |
| no Bi, Cu | 12 | 0.5 | 1.5 | 2.1 | 0.0 | 0.0 | 0.3 | 0.3 | 0.2 |
| no Bi, Sb | 12 | 0.5 | 1.5 | 2.1 | 0.0 | 0.1 | 0.0 | 0.3 | 0.1 |
| no Bi, B | 12 | 0.5 | 1.5 | 2.1 | 0.0 | 0.1 | 0.3 | 0.0 | 0.2 |
| no Cu, Sb | 12 | 0.5 | 1.5 | 2.1 | 0.15 | 0.0 | 0.0 | 0.3 | 0.2 |
| no Cu, B | 12 | 0.5 | 1.5 | 2.1 | 0.15 | 0.0 | 0.3 | 0.0 | 0.4 |
| no Sb, B | 12 | 0.5 | 1.5 | 2.1 | 0.15 | 0.1 | 0.0 | 0.0 | 0.6 |
| only Bi | 12 | 0.5 | 1.5 | 2.1 | 0.15 | 0.0 | 0.0 | 0.0 | 0.4 |
| only Cu | 12 | 0.5 | 1.5 | 2.1 | 0.0 | 0.1 | 0.0 | 0.0 | 0.4 |
| only Sb | 12 | 0.5 | 1.5 | 2.1 | 0.0 | 0.0 | 0.3 | 0.0 | 0.1 |
| only B | 12 | 0.5 | 1.5 | 2.1 | 0.0 | 0.0 | 0.0 | 0.3 | 0.3 |
| no promoters | 12 | 0.5 | 1.5 | 2.1 | 0.0 | 0.0 | 0.0 | 0.0 | 0.3 |
| K | 12 | 0.5 | 1.5 | $K_{2.1}$ | 0.15 | 0.1 | 0.3 | 0.3 | 0.25 |
| Rb | 12 | 0.5 | 1.5 | $Rb_{2.1}$ | 0.15 | 0.1 | 0.3 | 0.3 | 0.29 |

Lifetime Tests

Lifetime tests of a low Cs content catalyst ($Cs_{1.0}$) and a high Cs content catalyst ($Cs_{2.1}$) are shown in FIGS. 6A-1 and 6A-2. Both catalysts were tested in an "accelerated" lifetime test; that is, at 300° C. catalyst temperature and with feed flowrates higher than normal conditions (W/F=400-500 $g_{cat}$*hr/$mol_{MAC}$). It can be seen that the high Cs catalyst shows a more stable performance than the low Cs catalyst; i.e. less decline in conversion and less decline in relative activity.

Another set of lifetime tests of a low Cs content catalyst ($Cs_{1.0}$) and a high Cs content catalyst ($Cs_{2.1}$) is shown in FIG. 6B. These tests were conducted at 290° C., with "normal" feed flowrates (W/F=825 $g_{cat}$*hr/$mol_{MAC}$). The ratio of relative activity over its initial relative activity (a/ao) is plotted against time on stream. It can be seen that high Cs catalyst shows a stable performance and the low Cs catalyst does not.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letter of patent of the United States of America is:

1. A catalyst comprising a heteropoly acid compound of the general formula:

$$Mo_{12}V_aP_bCs_cBi_dCu_eSb_fO_x$$

where Mo is molybdenum, V is vanadium, P is phosphorus, Cs is cesium, Bi is bismuth, Cu is copper, Sb is antimony and O is oxygen, a is 0.01 to 5.0, b is 0.5 to 3.5, c is 1.5 to 2.75, d is 0.05 to 0.5, e is 0.05 to 0.5, f is 0.1 to 0.5 and x satisfies the valences.

2. The catalyst of claim 1 wherein the heteropoly acid compound contains one or more element selected from the group consisting of boron, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum.

3. The catalyst of claim 1 wherein the heteropoly acid compound has the general formula:

$$Mo_{12}V_aP_bCs_cBi_dCu_eSb_fM'_gO_x$$

where Mo is molybdenum, V is vanadium, P is phosphorus, Cs is cesium, Bi is bismuth, Cu is copper, M' is one or more of boron, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum, O is oxygen, a is 0.01 to 5.0, b is 0.5 to 3.5, c is 1.5 to 2.75, d is 0.05 to 0.5, e is 0.05 to 0.5, f is 0.1 to 0.5, g is 0 to 0.5 and x satisfies the valences.

4. The catalyst of claim 1 wherein c is greater than 1.5 to 2.75.

5. The catalyst of claim 1 wherein c is 2.0 to 2.75.

6. A process of preparing a heteropoly acid compound catalyst comprising:
    a) mixing the solution of a molybdenum compound, a vanadium compound, a phosphorus compound, a cesium compound, a bismuth compound, a copper compound and an antimony compound;
    b) precipitating solid particles
    c) removing liquid to leave the solid particles;
    d) drying the solid particles;
    e) calcining the solid particles; and
    f) forming a heteropoly acid compound catalyst comprising the general formula:

$$Mo_{12}V_aP_bCs_cBi_dCu_eSb_fO_x$$

where Mo is molybdenum, V is vanadium, P is phosphorus, Cs is cesium, Bi is bismuth, Cu is copper, Sb is antimony and O is oxygen, a is 0.01 to 5.0, b is 0.5 to 3.5, c is 1.5 to 2.75, d is 0.05 to 0.5, e is 0.05 to 0.5, f is 0.1 to 0.5 and x satisfies the valences.

7. The process of claim 6 wherein the molybdenum compound is ammonium paramolybdate, molybdenum trioxide, molybdenum chloride or mixtures or combinations thereof, the vanadium compound is ammonium metavanadate, vanadium pentoxide, vanadium chloride or mixtures or combinations thereof, the phosphorus compound is phosphoric acid, ammonium phosphite or mixtures or combinations thereof, the copper compound is copper nitrate, copper chloride or mixtures or combinations thereof, the bismuth compound is bismuth nitrate, bismuth oxide, bismuth chloride or mixtures or combinations thereof, the cesium compound is cesium nitrate, cesium oxide, cesium chloride or mixtures or combinations thereof and the antimony compound is antimony nitrate, antimony oxide, antimony chloride or mixtures or combinations thereof.

8. The process of claim 6 wherein calcining is at a temperature of about 350° C. to about 450° C. for about 2 to about 12 hours.

9. The process of claim 6 wherein calcining is in two stages, one at a temperature lower than about 350° C. for about 1 to about 8 hours and another at a temperature above about 350° C. for about 2 to about 12 hours.

10. The process of claim 6 wherein c is greater than 1.5 to 2.75.

11. A process for converting saturated and/or unsaturated aldehydes to unsaturated carboxylic acids comprising contacting a saturated and/or unsaturated aldehyde with an oxidizing agent in the presence of a supported or bound heteropoly acid catalyst comprising a heteropoly acid compound comprising the general formula:

$$Mo_{12}V_aP_bCs_cBi_dCu_eSb_fO_x$$

where Mo is molybdenum, V is vanadium, P is phosphorus, Cs is cesium, Bi is bismuth, Cu is copper, Sb is antimony and O is oxygen, a is 0.01 to 5.0, b is 0.5 to 3.5, c is 1.5 to 2.75, d is 0.05 to 0.5, e is 0.05 to 0.5, f is 0.1 to 0.5 and x satisfies the valences.

12. The process of claim 11 wherein the oxidizing agent is air or another oxygen-containing gas.

13. The process of claim 11 wherein the oxygen-containing gas additionally comprises nitrogen, carbon dioxide, noble gases or steam.

14. The process of claim 11 wherein pressure is from about 0 atm to about 5 atm.

15. The process of claim 11 wherein the pressure is about 1 atm.

16. The process of claim 11 wherein temperature is from about 230° C. to about 450° C.

17. The process of claim 11 wherein the temperature is from about 250° C. to about 400° C.

18. The process of claim 11 wherein the temperature is from about 250° C. to about 350° C.

19. The process of claim 11 wherein the unsaturated aldehyde is methacrolein.

20. The process of claim 11 wherein the saturated aldehyde is isobutanal or isobutyraldehyde.

* * * * *